(12) United States Patent
Chen et al.

(10) Patent No.: US 12,233,457 B2
(45) Date of Patent: Feb. 25, 2025

(54) THREE-DIMENSIONAL PRINTING

(71) Applicant: Hewlett-Packard Development Company, L.P., Spring, TX (US)

(72) Inventors: Tienteh Chen, San Diego, CA (US); Dennis Z. Guo, San Diego, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 796 days.

(21) Appl. No.: 17/047,503

(22) PCT Filed: Sep. 21, 2018

(86) PCT No.: PCT/US2018/052278
§ 371 (c)(1),
(2) Date: Oct. 14, 2020

(87) PCT Pub. No.: WO2020/060567
PCT Pub. Date: Mar. 26, 2020

(65) Prior Publication Data
US 2021/0354203 A1    Nov. 18, 2021

(51) Int. Cl.
*B33Y 70/00*     (2020.01)
*B22F 10/14*    (2021.01)
(Continued)

(52) U.S. Cl.
CPC ............. *B22F 10/64* (2021.01); *B22F 10/14* (2021.01); *B22F 10/20* (2021.01); *B33Y 10/00* (2014.12);
(Continued)

(58) Field of Classification Search
CPC .......... B22F 10/12; B22F 10/14; B22F 10/64; B29C 64/112; B29C 64/165; B33Y 10/00; B33Y 70/00; B33Y 70/10; C09D 175/04
See application file for complete search history.

(56) References Cited

U.S. PATENT DOCUMENTS

| | | |
|---|---|---|
| 5,510,066 A | 4/1996 | Fink et al. |
| 7,807,077 B2 | 10/2010 | Hochsmann et al. |

(Continued)

FOREIGN PATENT DOCUMENTS

| | | |
|---|---|---|
| EP | 2001656 | 10/2014 |
| EP | 1922349 | 8/2016 |
| WO | WO-2017046132 A1 | 3/2017 |

*Primary Examiner* — Vanessa T. Luk
(74) *Attorney, Agent, or Firm* — Dierker & Kavanaugh, P.C.

(57) ABSTRACT

Examples of a three-dimensional (3D) printing kit include a particulate build material and a binder fluid. The particulate build material includes from about 80 wt % to 100 wt % metal particles based on a total weight of the particulate build material. In some examples, the binder fluid includes water, polymer particles in an amount ranging from about 1 wt % to about 40 wt % based on a total weight of the binder fluid, and a blocked polyisocyanate adhesion promoter in an amount ranging from about 0.05 wt % to about 5 wt % based on the total weight of the binder fluid. In some other examples, the binder fluid includes water and the polymer particles, and the 3D printing kit further includes an adhesion promoter fluid which includes water and the blocked polyisocyanate adhesion promoter.

18 Claims, 3 Drawing Sheets

200 ↘

202 — Iteratively Applying Individual Build Material Layers of a Particulate Build Material which Includes from about 80 wt% to about 100 wt% Metal Particles Based on the Total Weight of the Particulate Build Material 204 — Based on a 3D Object Model, Selectively Applying Water, Polymer Particles, and a Blocked Polyisocyanate Adhesion Promoter to Individual Build Material Layers to Define Individually Patterned Layers of a 3D Intermediate Object 206 — Heating All of the Individually Patterned Layers to Deblock the Blocked Polyisocyanate Adhesion Promoter and Form a Crosslinked Network Among the Metal Particles in Patterned Portions of All of the Individually Patterned Layers, thereby Forming a 3D Intermediate Object

(51) Int. Cl.
*B22F 10/20* (2021.01)
*B22F 10/64* (2021.01)
*B33Y 10/00* (2015.01)
*B33Y 30/00* (2015.01)
*B29C 64/165* (2017.01)

(52) U.S. Cl.
CPC .............. *B33Y 30/00* (2014.12); *B33Y 70/00* (2014.12); *B29C 64/165* (2017.08)

(56) References Cited

U.S. PATENT DOCUMENTS

| | | |
|---|---|---|
| 9,453,142 B2 | 9/2016 | Rolland et al. |
| 2005/0049739 A1* | 3/2005 | Kramer .................. B33Y 10/00 700/198 |
| 2010/0234485 A1* | 9/2010 | Kohli Steck ....... C08G 18/6216 556/89 |
| 2016/0137839 A1* | 5/2016 | Rolland ................ C08G 18/42 522/71 |
| 2016/0200908 A1* | 7/2016 | Osaka .................... C08L 39/06 524/556 |
| 2018/0079134 A1 | 3/2018 | Tomko et al. |

* cited by examiner

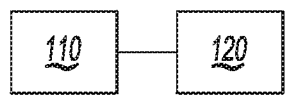
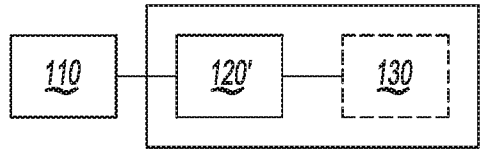
*Fig-1A*
*Fig-1B*
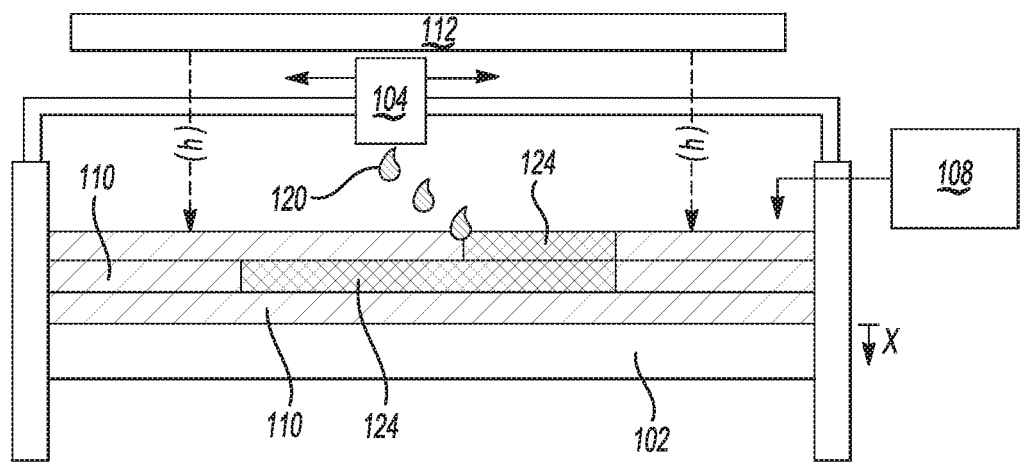
*Fig-2*
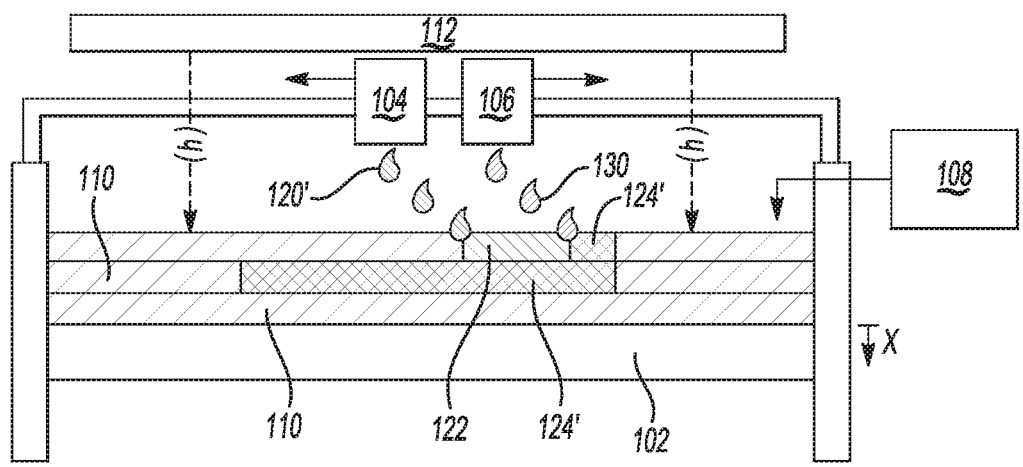
*Fig-3*

THREE-DIMENSIONAL PRINTING

BACKGROUND

Three-dimensional (3D) printing may be an additive printing process used to make three-dimensional solid parts from a digital model. 3D printing is often used in rapid product prototyping, mold generation, mold master generation, and short run manufacturing. Some 3D printing techniques are considered additive processes because they involve the application of successive layers of material (which, in some examples, may include build material, binder and/or other printing liquid(s), or combinations thereof). This is unlike traditional machining processes, which often rely upon the removal of material to create the final part. Some 3D printing methods use chemical binders or adhesives to bind build materials together. Other 3D printing methods involve at least partial curing, thermal merging/fusing, melting, sintering, etc. of the build material, and the mechanism for material coalescence may depend upon the type of build material used. For some materials, at least partial melting may be accomplished using heat-assisted extrusion, and for some other materials (e.g., polymerizable materials), curing or fusing may be accomplished using, for example, ultra-violet light or infrared light.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIGS. 1A and 1B schematically illustrate different examples of three-dimensional printing kits disclosed herein;

FIG. 2 graphically illustrates an example three-dimensional printing kit in use in accordance with an example three-dimensional printing method disclosed herein;

FIG. 3 graphically illustrates another example three-dimensional printing kit in use in accordance with another example three-dimensional printing method disclosed herein;

DETAILED DESCRIPTION

Figure 4:
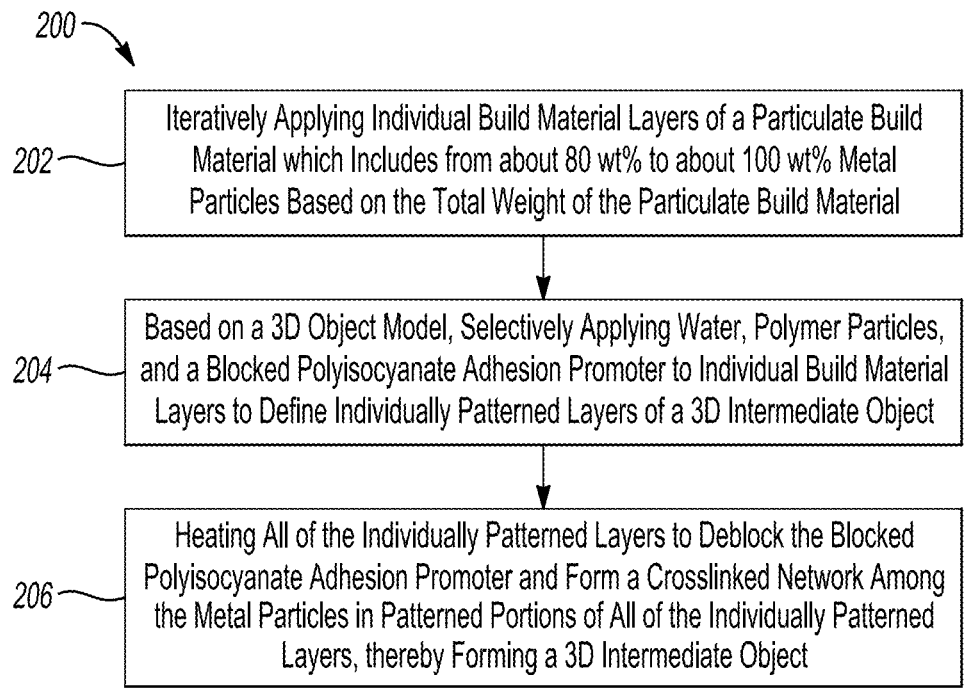
FIG. 4 is a flow diagram illustrating an example method of three-dimensional printing in accordance with the present disclosure.

In some examples of three-dimensional (3D) printing, a binder fluid is selectively applied to a layer of build material on a build platform, thereby patterning a selected region of the layer, and then another layer of the build material is applied thereon. The binder fluid is then selectively applied to this other layer, and these processes may be repeated to form a green part (referred to herein as "3D intermediate part" or "3D intermediate object") of a 3D part/object that is ultimately to be formed. The binder fluid may be capable of penetrating the layer of the build material onto which it is applied, and/or spreading around an exterior surface of the build material and filling void spaces between particles of the build material. The binder fluid can include binder particles, such as polymer latex particles, that when cured, temporarily hold the build material of the 3D intermediate part together. The 3D intermediate part may be moved from the build platform to a separate device for heating to remove the binder particles and to sinter the build material particles of the patterned intermediate part to form the 3D part/object.

While the binder particles temporarily hold the build material of the 3D intermediate part together, the 3D intermediate part may also contain air voids. As such, the patterned intermediate part may be porous, which can reduce its rigidity and increase its fragility. On the build platform, the 3D intermediate part may be supported by adjacent non-patterned build material. However, the fragility of the 3D intermediate part may make it difficult to move the patterned intermediate part from the build platform to the separate device for heating.

In the examples disclosed herein, a blocked polyisocyanate adhesion promoter is included in the binder fluid or is selectively applied (as part of a separate fluid) with the binder fluid onto the patterned layers. As such, both the blocked polyisocyanate adhesion promoter and the polymer particles are present in the patterned portions of the layers. The blocked polyisocyanate adhesion promoter is stable at room temperature, but dissociates to generate isocyanate functional groups (—N=C=O) when heated (e.g., at curing temperatures of the polymer particles). The deblocked polyisocyanate can react with many functional groups, such as an amine, a hydroxyl, a carboxylic, an amide, a urethane, etc. In an example, the deblocked poly(isocyanate)s can react with each other. In another example, the deblocked poly(isocyanate) can react with the functional groups (e.g., carboxylic functional groups, —COOH) on different polymer chains of the polymer particles. Deblocking and the subsequent crosslinking reactions can take place at mild thermal curing conditions (e.g., the curing temperature of the polymer particles). The crosslinking reaction between the different deblocked isocyanate functional groups and, in some instances, the deblocked isocyanate functional groups and the polymer particle functional groups forms a three-dimensional polymer (crosslinked) network among the build material particles. It has been found that the crosslinked network formed from the deblocked polyisocyanate adhesion promoter increases the tensile strength of the 3D intermediate part, which enhances its robustness and stability. Enhanced robustness and stability can render the patterned intermediate part strong enough to withstand extraction from the build platform and handling during transfer to the separate heating device.

As such, as used herein, the term "3D intermediate part" or "3D intermediate object" or "patterned intermediate part/object" refers to an intermediate part that has a shape representative of the final 3D printed part/object, and that includes build material particles that are bound together by a crosslinked network. It is to be understood that any build material that is not patterned with the binder fluid or the binder fluid and the separate adhesion promoter is not considered to be part of the 3D intermediate part, even if it is adjacent to or surrounds the 3D intermediate part. For example, unprinted (non-patterned) particulate build material acts to support the 3D intermediate part while contained therein, but the non-patterned particulate build material is not part of the 3D intermediate part unless it is printed with binder fluid (or binder fluid along with an adhesion promoter fluid).

Also as used herein, "sinter" means to coalesce the build material into a solid or porous mass by heating it. In other words, sintering refers to the joining of the material of adjacent particles, and can include complete joining of the material into a common structure. In some instances, sintering takes place without liquefaction of the build material. It is to be understood, however, that sintering may involve fusing, annealing, melting, etc. depending, in part, upon the build material used.

In accordance with this, the examples disclosed herein include three-dimensional printing kits, multi-fluid kits for three-dimensional printing, and methods for three-dimensional printing.

One example of the three-dimensional printing kit can include: a particulate build material including from about 80 wt % to 100 wt % metal particles based on a total weight of the particulate build material; and a binder fluid including water, polymer particles in an amount ranging from about 1 wt % to about 40 wt % based on a total weight of the binder fluid, and a blocked poly(isocyanate) adhesion promoter in an amount ranging from about 0.05 wt % to about 5 wt % based on the total weight of the binder fluid.

One example of a multi-fluid kit for three-dimensional printing can include: a binder fluid including water, and polymer particles in an amount ranging from about 1 wt % to about 40 wt % based on a total weight of the binder fluid; and an adhesion promoter fluid including water, and a blocked poly(isocyanate) adhesion promoter in an amount of from about 0.1 wt % to about 15 wt % based on a total weight of the adhesion promoter fluid. This multi-fluid kit may also be included in a three-dimensional printing kit, which also includes a particulate build material including from about 80 wt % to 100 wt % metal particles based on a total weight of the particulate build material.

One example of the method can include: iteratively applying individual build material layers of a particulate build material which includes from about 80 wt % to 100 wt % metal particles based on a total weight of the particulate build material; based on a 3D object model, selectively applying water, polymer particles, and a blocked poly(isocyanate) adhesion promoter to individual build material layers to define individually patterned layers; and heating all of the individually patterned layers to deblock the blocked poly(isocyanate) adhesion promoter and form a crosslinked network among the metal particles in patterned portions of all of the individually patterned layers, thereby forming a 3D intermediate object. As will be described in detail herein, the blocked poly(isocyanate) adhesion promoter may be selectively applied as part of a binder fluid including water and the polymer particles; or as part of an adhesion promoter fluid that is separate relative to the binder fluid.

It is noted that when discussing the three-dimensional printing kits and methods herein, each of these discussions can be considered applicable to one another whether or not they are explicitly discussed in the context of a particular example. Thus, for example, when discussing a binder fluid related to a three-dimensional printing kit, such disclosure is also relevant to and directly supported in the context of other three-dimensional printing kits, methods of three-dimensional printing, vice versa, etc.

It is also understood that terms used herein will take on their ordinary meaning in the relevant technical field unless specified otherwise. In some instances, there are terms defined more specifically throughout the specification, and thus, these terms have a meaning as described herein.

Particulate Build Materials

In examples of the 3D printing kits and methods disclosed herein, the build material can include any particulate build material that includes from about 80 wt % to 100 wt % of metal particles based on the total weight of the particulate build material. In other examples, the metal particles can be present in the particulate build material in amounts ranging from about 90 wt % to 100 wt %, or from about 95 wt % to 100 wt %, or in an amount of about 100 wt %. When the metal particles are present in the particulate build material in an amount less than 100 wt %, the remainder of the particulate build material may be made up of additives, such as flow aids (e.g., in amounts ranging from about 0.05 wt % to about 0.2 wt %), filler materials, such as plastic powder, etc.

In some examples, the metal particles may be uncoated metal particles. By "uncoated", it is meant that the metal particles do not have a polymeric coating formed thereon. The metal particles may, however, have a naturally formed metal oxide layer at its surface. In some examples, the particulate build material is devoid of a polymer resin (i.e., no polymer resin, either as a coating on the metal particles or separate from the metal particles is included).

In an example, the metal particles are a single phase metallic material composed of one element. In this example, the sintering temperature may be below the melting point of the single element. In another example, the metal particles are composed of two or more elements, which may be in the form of a single phase metallic alloy or a multiple phase metallic alloy. In these other examples, sintering generally occurs over a range of temperatures. With respect to alloys, materials with a metal alloyed to a non-metal (such as a metal-metalloid alloy) can be used as well.

In the examples disclosed herein, the particulate build material can include metal particles selected from the group consisting of aluminum, aluminum alloys, titanium, titanium alloys, copper, copper alloys, cobalt, cobalt alloys, chromium, chromium alloys, nickel, nickel alloys, vanadium, vanadium alloys, tin, tin alloys, tungsten, tungsten alloys, tungsten carbide, tantalum, tantalum alloys, molybdenum, molybdenum alloys, magnesium, magnesium alloys, gold, gold alloys, silver, silver alloys, zirconium, zirconium alloys, ferrous alloys, stainless steel, steel, and an admixture thereof. Specific alloy examples can include AlSi 10 Mg, 2xxx series aluminum, 4xxx series aluminum, CoCr MP1, CoCr SP2, Maraging steel MS1, HASTELLOY™ C, HASTELLOY™ X, NickelAlloy HX, INCONEL™ IN625, INCONEL™ IN718, stainless steel GP1, stainless steel 17-4PH, stainless steel 316L, stainless steel 430L titanium 6AI4V, and titanium 6AI-4V ELI7. While several example alloys have been provided, it is to be understood that other alloys may be used.

The temperature(s) at which the metal particles of the particulate build material sinter together is/are above the temperature of the environment in which the patterning portion of the 3D printing method is performed, e.g., patterning at from about 18° C. to about 300° C. and sintering (which may include de-binding and sintering) at from about 500° C. to about 3,500° C. In some examples, the metal particles may have a melting point ranging from about 500° C. to about 3,500° C. In other examples, the metal particles may be an alloy having a range of melting points.

The particle size of the particulate build material, and in particular of the metal particles, can be similarly sized or differently sized. In one example, the D50 particle size of the particulate build material can range from 0.5 µm to 200 µm. In some examples, the metal particles can have a D50 particle size distribution value that can range from about 2 µm to about 150 µm, from about 1 µm to about 100 µm, from about 1 µm to about 50 µm, etc. Individual particle sizes can be outside of these ranges, as the "D50 particle size" is defined as the particle size at which about half of the particles are larger than the D50 particle size and about half of the other particles are smaller than the D50 particle size (by weight based on the metal particle content of the particulate build material).

As used herein, "particle size" refers to the value of the diameter of spherical particles, or, for particles that are not spherical, can refer to the longest dimension of that non-spherical particle. The particle size can be presented as a Gaussian distribution or a Gaussian-like distribution (or normal or normal-like distribution). Gaussian-like distributions are distribution curves that may appear essentially Gaussian in their distribution curve shape, but which can be slightly skewed in one direction or the other (toward the smaller end or toward the larger end of the particle size distribution range). That being stated, an example Gaussian-like distribution of the metal particles can be characterized generally using "D10," "D50," and "D90" particle size distribution values, where D10 refers to the particle size at the $10^{th}$ percentile, D50 refers to the particle size at the $50^{th}$ percentile, and D90 refers to the particle size at the $90^{th}$ percentile. For example, a D50 value of 25 μm means that 50% of the particles (by number) have a particle size greater than 25 μm and 50% of the particles have a particle size less than 25 μm. Particle size distribution values are not necessarily related to Gaussian distribution curves, but in one example of the present disclosure, the metal particles can have a Gaussian distribution, or more typically a Gaussian-like distribution with offset peaks at about D50. In practice, true Gaussian distributions are not typically present, as some skewing can be present, but still, the Gaussian-like distribution can be considered to be essentially referred to as "Gaussian" as used conventionally. In yet other examples, the particles can have a D50 particle size distribution value of from about 2 μm to about 100 μm, from about 5 μm to about 75 μm, from about 25 μm to about 50 μm, from about 5 μm to about 15 μm, or from about 3 μm to about 10 μm. The shape of the particles of the particulate build material can be spherical, non-spherical, random shapes, or a combination thereof.

Blocked Polyisocyanate Adhesion Promoter

To bind the particulate build material on a layer by layer basis and form a patterned intermediate part, binder fluid with polymer particles can be used. In the examples disclosed herein, the tensile strength of the patterned intermediate part formed using the particulate build material and the polymer particles can be enhanced using a blocked poly (isocyanate) adhesion promoter.

Blocked polyisocyanate adhesion promoters are characterized as oligomers or polymers that include two or more isocyanate functional groups that are linked to a chemical moiety that renders the isocyanate non-reactive. The blocked polyisocyanate may be aromatic or aliphatic. The isocyanate groups of the blocked polyisocyanate adhesion promoter can become reactive as crosslinkers after being deblocked during the 3D printing and curing process, but within the binder fluid or the separate adhesion promoter fluid, the isocyanate groups can remain stable due to the blocking group that is attached to the isocyanate(s). Thus, the term "blocked polyisocyanate" refers to compounds with multiple isocyanate groups where a plurality of the isocyanate groups are coupled to a chemical moiety that stabilizes the isocyanate groups in the binder fluid or the separate adhesion promoter fluid so that they remain available for reaction after printing on the particulate build material.

The chemical moiety that prevents the isocyanate groups from reacting in the binder fluid or the separate adhesion promoter can be referred to herein as a "blocking group." To convert the blocked polyisocyanate to a reactive isocyanate species, the blocking group can be dissociated from isocyanate groups to result in a "deblocked polyisocyanate." Deblocking can occur by heating the blocked polyisocyanate to a temperature where dissociation of the blocking group can occur, e.g., typically at from 100° C. to 200° C. There are deblocking or dissociation temperatures outside of this range, e.g., at lower temperatures, but in accordance with examples of the present disclosure, higher temperature deblocking can, in some examples, have the added benefit of accelerating the crosslinking process. Deblocking of the blocked polyisocyanate can occur according to Formula I, where the blocking group B is dissociated and the free isocyanate is formed:

Formula I

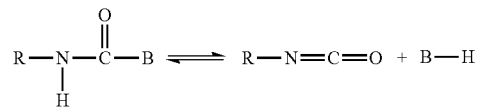

Once free isocyanate(s) is/are formed, there are many reactions that may take place. Some possible reactions that can take place after deblocking are shown in the reaction Scheme 1.

Scheme 1

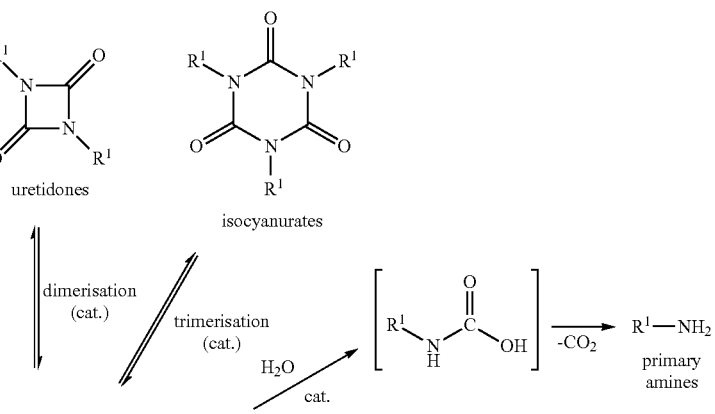

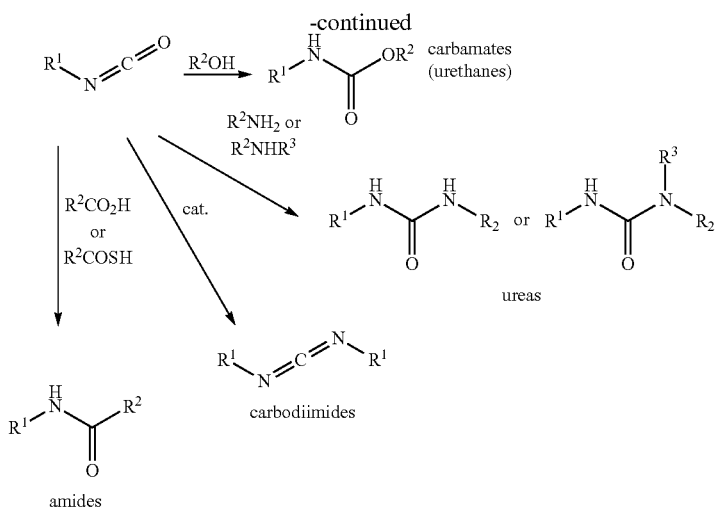

Most likely, the free isocyanate(s) will react to form dimer(s) or trimer(s) and generate a crosslinked polymer matrix or network. In some examples, the free isocyanate(s) have a reactivity towards other functional groups in the deblocked polyisocyanate compound or towards corresponding groups (e.g., by self-condensation or self-addition) in another deblocked polyisocyanate compound. Examples of these side reactions can result in the formation of a uretdione, an isocyanurate (a triazine ring), an allophanate, or a biuret.

The free isocyanate(s) may also react with carboxylic (COOH) functional group(s) of the polymer particles in the binder fluid to form amides. Because the blocked polyisocyanate deblocks to generate the reactive isocyanate species, one deblocked polyisocyanate compound can react with carboxylic functional groups on different polymer chains of the polymer particles, thereby chemically bonding them together to form amide linkages. This additional coupling can further densify the crosslinked network structure.

Furthermore, the free isocyanate(s) may also react with the metal oxide at the surface of the metal particles of the particulate build material, which enhances the adhesion between metal particles and polymer particles in the binder fluid.

Thus, in many instances, the application of the blocked polyisocyanate adhesion promoter, along with polymer particles, to layers of particulate build material, and their subsequent deblocking and reaction can enhance the tensile strength of the resulting patterned intermediate part. This is particularly useful when the patterned intermediate part, formed through an additive layer by layer printing process, is to be moved into an oven for sintering. Without sufficient tensile strength, patterned intermediate parts can become damaged during the move from any the (non-solidified) particulate build material on the build platform to the fusing oven, particularly if the patterned intermediate part is large or complex.

In the examples disclosed herein, the blocked polyisocyanate includes blocking groups selected from the group consisting of a phenol blocking group, a lactam blocking group, an oxime blocking group, an azole blocking group, a diketene blocking group, a formate blocking group, and combinations thereof. Some specific examples of blocking groups include ε-caprolactam, butanone oxime, diethyl malonate, 1,2,3-triazole, 1,2,4-triazole, pyrazoles, imidazoline, and combinations thereof. Butanone oxime is also known as methyl ethyl ketoxime. An example of a suitable pyrazole is 3,5-dimethyl pyrazole.

In an example, the blocked polyisocyanate crosslinker is a cationic blocked polyisocyanate. This blocked polyisocyanate does not have an acid number. One example of a cationic blocked polyisocyanate that can be used is VESTANAT® EP-DS 1076 (an acetoneoxime blocked polyisocyanate based on isophorone diisocyanate commercially available from Evonik Industries (Germany)).

In another example, the blocked polyisocyanate crosslinker is an anionic blocked polyisocyanate or a non-ionic blocked polyisocyanate. In one example, the anionic or non-ionic blocked polyisocyanate crosslinker can include a blocked polyisocyanate trimer. The blocked polyisocyanate trimer can have the structure shown in Formula II, as follows:

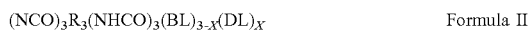

$$(NCO)_3R_3(NHCO)_3(BL)_{3-X}(DL)_X \qquad \text{Formula II}$$

where R can independently include a C2 to C10 branched or straight-chained alkyl, C6 to C20 alicyclic, C6 to C20 aromatic, or a combination thereof; BL can include a blocking group such as a phenol blocking group, a lactam blocking group, an oxime blocking group, an azole blocking group, a diketene blocking group, a formate blocking group, or a combination thereof; x can be from 0 to 1; and DL can include an anionic or non-ionic hydrophilic dispersing group.

More specific examples of the R groups include those present to complete isophorone diisocyanate (IPDI) trimers, e.g., methylated alicyclic R groups (sometimes also referred to as cycloaliphatic groups) such as present in N,N',N"-Tris (5-isocyanato-1,3,3-trimethylcyclohexylmethyl)-2,4,6-triketohexahydrotriazine; or hexanemethylene-1,6-diisocyanate (HDI) trimers, e.g., where R may be C2 to C10 alkyl, C2 to C8 alkyl, C2 to C6 alkyl, C3 to C8 alkyl, C4 to C8 alkyl, or C4 to C10 alkyl.

The hydrophilic dispersing group DL can be an anionic or a non-ionic hydrophilic group that can assist with dispersing the blocked polyisocyanate in the binder fluid or the separate adhesion promoter fluid. If DL is present, it can be present (represented by "x" in Formula II) at from greater than 0 to 1, or from 0.1 to 1, or from 0.25 to 1, or from 0.5 to 1, or from 0.1 to 0.5, for example. The concentration of DL present can depend on the concentration useful for suspending the blocked polyisocyanate in the binder fluid or the separate adhesion promoter fluid.

In one example of Formula II, the blocking group, once liberated (as BL-H) can be ε-caprolactam, butanone oxime, or 3,5-dimethyl pyrazole, for example.

In another, more specific example of Formula II, x can be from greater than 0 to 1, BL can be a dimethylpyrazole, DL can be N-(2-aminoethyl)-beta-alanine or a salt thereof, and R can be C4 to C8 alkyl or C8 to C14 methylated alicyclic group. In this example, because N-(2-aminoethyl)-beta-alanine is present, x is greater than 0, e.g., from 0.1 to 1.

An example of a suitable blocked polyisocyanate trimer has the structure shown in Formula III, as follows:

Formula III

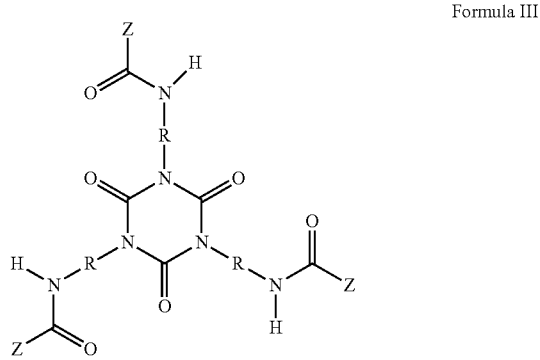

where R is independently a C2 to C10 branched or straight-chained alkyl, C6 to C20 alicyclic, C6 to C20 aromatic, or a combination thereof; and Z is $(BL)_{3-x}(DL)_x$, wherein BL is selected from the group consisting of a phenol blocking group, a lactam blocking group, an oxime blocking group, an azole blocking group, a diketene blocking group, a formate blocking group, and combinations thereof; x is from 0 to 1; and DL is an anionic or a non-ionic hydrophilic dispersing group. As such, Z independently includes a blocking group (the "BL" groups described herein), a hydrophilic dispersing group (the "DL" groups described herein), or a combination of both. In other words, Z in Formula III represents "$(BL)_{3-x}(DL)_x$" in Formula II. In some examples, the three independent Z groups shown in Formula III can represent from 2 to 3 blocking groups (BL) and from 0 to 1 hydrophilic dispersing groups (DL) per trimer molecule. Thus, with specific reference to Z in Formula III, there may be some specific individual molecules in the binder fluid or the separate adhesion promoter fluid with three BL groups, and other individual molecules within the in the binder fluid or the separate adhesion promoter fluid that include less than three BL groups. Thus, in some examples, there may be no hydrophilic dispersing groups, and in other examples there may be from 0.1 to 1 hydrophilic dispersing groups.

Some specific examples of commercially available anionic blocked polyisocyanates that can be used include IMPRAFIX® 2794 from Covestro (an HDI trimer blocked by 3,5-dimethyl pyrazole and further includes N-(2-aminoethyl)-beta-alaninate; acid number of 10 mg KOH/g) and BAYHYDUR® BL XP 2706 from Covestro (blocked aliphatic polyisocyanate, acid number of 32 mg KOH/g). IMPRAFIX® 2794 can be deblocked at about 130° C.

Some specific examples of commercially available non-ionic blocked polyisocyanates that can be used include Matsui FIXER™ WF-N from Matsui Shikiso Chemical (a 3,5-dimethyl pyrazole non-ionic blocked polyisocyanate) and TRIXENE® Aqua BI 220 from Baxenden (non-ionic aliphatic water-dispersed blocked isocyanate). Matsui FIXER™ WF-N can be deblocked at about 150° C.

Other example blocked polyisocyanates that can be used include, for example BAYHYDUR® BL 2867, BAYHYDUR® BL 2781, BAYHYDUR® BL 5335, BAYBOND® XL 6366 XP, BAYBOND® XL 825, BAYBOND® XL 7270, BAYBOND® XL 3674 XP, each of which is from Covestro or VESTANAT® EP-DS 1205 E from Evonik.

The blocked polyisocyanate crosslinker in the binder fluid or the separate adhesion promoter fluid is deblocked during the curing process (e.g., after patterning, i.e., after the fluid(s) are applied to the particulate build material in the fabrication bed), and thus is available for crosslinking during the curing process. As mentioned herein, the deblocked polyisocyanate crosslinker can self-crosslink and/or crosslink the functional group(s) of the polymer particles in the binder fluid and/or can crosslink the functional group(s) of itself and/or another deblocked polyisocyanate crosslinker. The crosslinking between the deblocked isocyanates, alone or along with the chains of the polymer particles forms a strong polymer network among the metal particles of the particulate build material.

Polymer (Latex) Particles and Other Polymer Additives

As mentioned above, to bind the particulate build material on a layer by layer basis and form a 3D intermediate part, binder fluid with polymer particles can be used. The following discussion relates particularly to the polymer particles that can be used in the binder fluid. In some examples, the polymer particles are latex particles, which refer to any polymer (homopolymer, co-polymer, or heteropolymer) dispersed in an aqueous medium.

The polymer particles may have several different morphologies. In one example, the polymer particles can include two different copolymer compositions, which may be fully separated core-shell polymers, partially occluded mixtures, or intimately comingled as a polymer solution. In another example, the polymer particles can be individual spherical particles containing polymer compositions of hydrophilic (hard) component(s) and/or hydrophobic (soft) component(s) that can be interdispersed. In one example, the interdispersion can be according to IPN (interpenetrating networks) although it is contemplated that the hydrophilic and hydrophobic components may be interdispersed in other ways. In yet another example, the polymer particles can be composed of a hydrophobic core surrounded by a continuous or discontinuous hydrophilic shell. For example, the particle morphology can resemble a raspberry, in which a hydrophobic core can be surrounded by several smaller hydrophilic particles that can be attached to the core. In yet another example, the polymer particles can include 2, 3, or 4 or more relatively large polymer particles that can be attached to one another or can surround a smaller polymer core. In a further example, the polymer particles can have a single phase morphology that can be partially occluded, can be multiple-lobed, or can include any combination of any of the morphologies disclosed herein.

In some examples, the polymer particles have carboxylic functional groups that can react with the free isocyanates. In these examples, it is to be understood that the monomer used to form a homopolymer, or at least one of the monomers used to form a heteropolymer or copolymer includes a carboxylic functional group.

Examples of monomers that include a carboxylic functional group include acrylic acid, methacrylic acid, ethacrylic acid, dimethylacrylic acid, maleic acid, cyanoacrylic acid, vinylacetic acid, allylacetic acid, crotonoic acid, fumaric acid, itaconic acid, sorbic acid, angelic acid, cinnamic acid, styrylacrylic acid, citraconic acid, glutaconic acid, aconitic acid, phenylacrylic acid, acryloxypropionic acid, vinylbenzoic acid, mesaconic acid, N-methacroyl-L-alanine, acrylamido glycolic acid, acryloxyethyl carboxylic acid, or the like.

In other examples, the polymer particles have amine functional groups that can react with the free isocyanates. In these examples, it is to be understood that the monomer used to form a homopolymer, or at least one of the monomers used to form a heteropolymer or copolymer includes an amine functional group. Examples of monomers that include an amine functional group include N-(3-Aminopropyl)methacrylamide, 2-Aminoethyl methacrylate, 2-Aminopropyl methacrylate, etc.

It is to be further understood that polymer particles with carboxylic functional groups are not included in the same binder fluid as polymer particles with amine functional groups.

Any of the monomers that include a carboxylic functional group or the monomers that include an amine functional group may be polymerized to form a homopolymer, or may be combined with one or more of the following monomers to form a heteropolymer or copolymer. In an example, a heteropolymer can include a hydrophobic component and a hydrophilic component. In this example, the heteropolymer can include a hydrophobic component that can include from about 65% to about 99.9% (by weight of the heteropolymer), and a hydrophilic component that can include from about 0.1% to about 35% (by weight of the heteropolymer). In one example, the hydrophobic component can have a lower glass transition temperature than the hydrophilic component.

The monomers that include the carboxylic functional group are acidic monomers that have a relatively high glass transition temperature ($T_g$), and can be used to form the hydrophilic component of a heteropolymer. In some examples, the acidic monomer content (which includes the carboxylic-containing monomer) can range from 0.1 wt % to 5 wt %, from 0.5 wt % to 3 wt %, or from 1 wt % to 5 wt % of the polymer particles with the remainder of the polymer particle being composed of non-acidic monomers. Other acidic monomers may be used in addition to the carboxylic-containing monomer. Examples of other suitable acidic monomers include maleic anhydride, vinylsulfonate, N-vinylsuccinamidic acid, sulfoethyl methacrylic acid, sulfopropyl acrylic acid, styrene sulfonic acid, sulfoethylacrylic acid, 2-methacryloyloxymethane-1-sulfonic acid, 3-methacryoyloxypropane-1-sulfonic acid, 3-(vinyloxy)propane-1-sulfonic acid, ethylenesulfonic acid, vinyl sulfuric acid, 4-vinylphenyl sulfuric acid, ethylene phosphonic acid, vinyl phosphoric acid, vinyl benzoic acid, 2-acrylam ido-2-methyl-1-propanesulfonic acid, combinations thereof, derivatives thereof, or mixtures thereof. Other examples of high $T_g$ hydrophilic monomers can include acrylamide, methacrylamide, monohydroxylated monomers, monoethoxylated monomers, polyhydroxylated monomers, or polyethoxylated monomers.

Examples of monomers that may be used to form the hydrophobic component of the heteropolymer polymer particles include C4 to C8 alkyl acrylates or methacrylates, styrene, substituted methyl styrenes, polyol acrylates or methacrylates, vinyl monomers, vinyl esters, ethylene, maleate esters, fumarate esters, itaconate esters, or the like. Some specific example monomers can include, C1 to C20 linear or branched alkyl (meth)acrylate, alicyclic (meth) acrylate, alkyl acrylate, styrene, methyl styrene, polyol (meth)acrylate, hydroxyethyl (meth)acrylate, or a combination thereof. In one specific class of examples, the polymer particles can be a styrene (meth)acrylate copolymer. In still another example, the polymer particles can include a copolymer with copolymerized methyl methacrylate being present at about 50 wt % or greater, or copolymerized styrene being present at about 50 wt % or greater. Both can be present, with one or the other at about 50 wt % or greater in a more specific example.

The term "(meth)acrylate" or "(meth)acrylic acid" or the like refers to monomers, copolymerized monomers, etc., that can either be acrylate or methacrylate (or a combination of both), or acrylic acid or methacrylic acid (or a combination of both). In some examples, the terms "(meth)acrylate" and "(meth)acrylic acid" can be used interchangeably, as acrylates and methacrylates are salts and esters of acrylic acid and methacrylic acid, respectively. Furthermore, mention of one compound over another can be a function of pH. Furthermore, even if the monomer used to form the polymer was in the form of a (meth)acrylic acid during preparation, pH modifications during preparation or subsequently when added to an ejectable fluid, such as a binder fluid, can impact the nature of the moiety as well (acid form vs. salt or ester form). Thus, a monomer or a moiety of a polymer described as (meth)acrylic acid or as (meth)acrylate should not be read so rigidly as to not consider relative pH levels, ester chemistry, and other general organic chemistry concepts.

In still other examples, the polymer particles in the binder fluid include polymerized monomers of vinyl acetate, vinyl chloride, vinylidene chloride, vinylbenzyl chloride, vinyl ester, vinyl pyrrolidone, styrene, ethylene, maleate esters, fumarate esters, itaconate esters, α-methyl styrene, p-methyl styrene, methyl methacrylate, hexyl acrylate, hexyl methacrylate, hydroxyethyl acrylate, butyl acrylate, butyl methacrylate, ethyl acrylate, ethyl methacrylate, propyl acrylate, propyl methacrylate, 2-ethylhexyl acrylate, 2-ethylhexyl methacrylate, octadecyl acrylate, octadecyl methacrylate, stearyl methacrylate, 2-phenoxyethyl methacrylate, vinylbenzyl chloride, isobornyl acrylate, tetrahydrofurfuryl acrylate, 2-phenoxyethyl methacrylate, benzyl methacrylate, benzyl acrylate, ethoxylated nonyl phenol methacrylate, isobornyl methacrylate, ethylene glycol dimethacrylate, diethylene glycol dimethacrylate, triethylene glycol dimethacrylate, cyclohexyl methacrylate, trimethyl cyclohexyl methacrylate, t-butyl methacrylate, n-octyl methacrylate, lauryl acrylate, lauryl methacrylate, trydecyl methacrylate, alkoxylated tetrahydrofurfuryl acrylate, isodecyl acrylate, dimethyl maleate, dioctyl maleate, acetoacetoxyethyl methacrylate, diacetone acrylamide, N-vinyl imidazole, N-vinylcarbazole, N-vinyl-caprolactam, pentaerythritol tri-acrylate, pentaerythritol tetra-acrylate, pentaerythritol tri-methacrylate, pentaerythritol tetra-methacrylate, glycidyl acrylate, glycidyl methacrylate, tetrahydrofuryl acrylate, tetrahydrofuryl methacrylate, diacetone acrylamide, t-butyl acrylamide, divinylbenzene, 1,3-butadiene, acrylonitrile, methacrylonitrile, combinations thereof, derivatives thereof, or mixtures thereof. These monomers include low glass transition temperature ($T_g$) monomers (lower relative to the $T_g$ of the acidic monomers) that can be used to form the hydrophobic component of a heteropolymer.

In an example, the selected monomer(s) can be polymerized to form a polymer, heteropolymer, or copolymer with a co-polymerizable dispersing agent. The co-polymerizable dispersing agent can be a polyoxyethylene compound, such as a HITENOL® compound (Montello Inc.) e.g., polyoxyethylene alkylphenyl ether ammonium sulfate, sodium polyoxyethylene alkylether sulfuric ester, polyoxyethylene styrenated phenyl ether ammonium sulfate, or mixtures thereof.

Any suitable polymerization process can be used. In some examples, an aqueous dispersion of polymer particles can be produced by emulsion polymerization or co-polymerization of any of the above monomers.

In one example, the polymer particles can be prepared by polymerizing high $T_g$ hydrophilic monomer(s) (including at least the carboxylic-containing monomer) to form the high $T_g$ hydrophilic component and attaching the high $T_g$ hydrophilic component onto the surface of the low $T_g$ hydrophobic component. In another example, the polymer particles can be prepared by polymerizing the low $T_g$ hydrophobic monomer(s) and the high $T_g$ hydrophilic monomer(s) (including at least the carboxylic-containing monomer) at a ratio of the low $T_g$ hydrophobic monomer(s) to the high $T_g$ hydrophilic monomer(s) that ranges from 5:95 to 30:70. In this example, the low $T_g$ hydrophobic monomer(s) can dissolve in the high $T_g$ hydrophilic monomer(s). In yet another example, the polymer particles can be prepared by polymerizing the low $T_g$ hydrophobic monomer(s), then adding the high $T_g$ hydrophilic monomer(s) (including at least the carboxylic-containing monomer). In this example, the polymerization process can cause a higher concentration of the high $T_g$ hydrophilic monomer(s) to polymerize at or near the surface of the low $T_g$ hydrophobic component. In still another example, the polymer particles can be prepared by copolymerizing the low $T_g$ hydrophobic monomers and the high $T_g$ hydrophilic monomer(s) (including at least the carboxylic-containing monomer), then adding additional high $T_g$ hydrophilic monomer(s). In this example, the copolymerization process can cause a higher concentration of the high $T_g$ hydrophilic monomers to copolymerize at or near the surface of the low $T_g$ hydrophobic component.

Other suitable techniques, specifically for generating a core-shell structure, can include grafting a hydrophilic shell onto the surface of a hydrophobic core, copolymerizing hydrophobic and hydrophilic monomers using ratios that lead to a more hydrophilic shell, adding hydrophilic monomer (or excess hydrophilic monomer) toward the end of the copolymerization process so there is a higher concentration of hydrophilic monomer copolymerized at or near the surface, or any other method can be used to generate a more hydrophilic shell relative to the core.

In one specific example, the low $T_g$ hydrophobic monomer(s) can be selected from the group consisting of C4 to C8 alkyl acrylate monomers, C4 to C8 alkyl methacrylate monomers, styrene monomers, substituted methyl styrene monomers, vinyl monomers, vinyl ester monomers, and combinations thereof; and the high $T_g$ hydrophilic monomers can be selected from the group consisting of at least one carboxylic-containing monomer, alone or in combination with other acidic monomers, unsubstituted amide monomers, alcoholic acrylate monomers, alcoholic methacrylate monomers, C1 to C2 alkyl acrylate monomers, C1 to C2 alkyl methacrylate monomers, and combinations thereof. The resulting polymer particles can exhibit a core-shell structure, a mixed or intermingled polymeric structure, or some other morphology.

In some examples, the polymer particles can have a weight average molecular weight (Mw, g/mol) that can range from about 5,000 Mw to about 2,000,000 Mw. In yet other examples, the weight average molecular weight can range from about 100,000 Mw to about 1,000,000 Mw, from about 100,000 Mw to about 500,000 Mw, from about 150,000 Mw to about 300,000 Mw, or from about 50,000 Mw to about 250,000 Mw. Weight average molecular weight (Mw) can be measured by Gel Permeation Chromatography with polystyrene standard.

In some examples, the polymer particles can be latent and can be activated by heat (which may be applied iteratively during 3D intermediate part formation or after 3D intermediate part formation). In these instances, the activation temperature can correspond to the minimum film formation temperature (MFFT) or a glass transition temperature ($T_g$) which can be greater than ambient temperature. As mentioned herein, "ambient temperature" may refer to room temperature (e.g., ranging about 18° C. to about 22° C.). In one example, the polymer particles can have a MFFT or $T_g$ that can be at least about 15° C. greater than ambient temperature. In another example, the MFFT or the $T_g$ of the bulk material (e.g., the more hydrophobic portion) of the polymer particles can range from about 25° C. to about 200° C. In another example, the particles can have a MFFT or $T_g$ ranging from about 40° C. to about 120° C. In yet another example, the polymer particles can have a MFFT or $T_g$ ranging from about 0° C. to about 150° C. In a further example, the polymer particles can have a $T_g$ that can range from about −20° C. to about 130° C., or in another example from about 60° C. to about 105° C. At a temperature above the MFFT or the $T_g$ of a latent polymer particle, the polymer latex particles can coalesce and can bind materials, such as the metal particles in the particulate build material.

The particle size of the polymer particles may depend upon the application in which the polymer particles are to be used. For example, to form the press bars described in the Example section herein, smaller particle size may be more desirable. In an example, the particle size of the polymer particles can range from about 1 nm to about 400 nm. In yet other examples, a particle size of the polymer particles can range from about 10 nm to about 300 nm, from about 50 nm to about 250 nm, from about 100 nm to about 250 nm, or from about 25 nm to about 250 nm. In some examples, the polymer particles can have a particle size that can be jetted via thermal ejection or printing, piezoelectric ejection or printing, drop-on-demand ejection or printing, continuous ejection or printing, etc. In these examples, the particle size of the polymer particles be about 100 nm or more.

In some examples, the polymer particles have a glass transition temperature higher than 60° C. and an average particle size of 1 nm or more.

In addition to the polymer (latex) particles, water soluble diol(s) or triol(s), water soluble diamine(s) or triamine(s), and water-borne polyol dispersions can be added to binder fluid to further enhance the crosslinking density and 3D intermediate part strength. Polyols are polymers or oligomers with two or more hydroxy functional group per polymer chain. Suitable types of polyols include polyether polyol, such as polypropylene polyol and polytetrahydrofuran polyol, aliphatic polyester polyol, aromatic polyester polyol, polycarbonate polyol, poly(ester-co-carbonate) polyol, acrylate polyol, polyurethane polyol, and polybutadiene polyol.

Examples of suitable water soluble diols or triols include ethylene glycol, diethylene glycol, triethylene glycol, tetraethylene glycol, trimethylol propane, 2-methyl-1,3-propanediol (MP diol), etc.

Examples of suitable water soluble diamines include ethylene diamine, propylene diamine, am inoethanol, etc. Some suitable commercially available examples include JEFFAMINE® D-230 (polyetheramine), JEFFAMINE® D-400 (polyetheramine), JEFFAMINE® D-2000 (polyoxypropylenediamine), etc. (each from Huntsman Chemicals).

Examples of suitable water borne polyol dispersions suitable include those in the BAYHYDROL® series, such as A2058, A2427, A2457, A2546, A2469, A2470, A2139, A2227, A2601, A2651, A2695, A2809, A2845, A2846, A 2861, U 2755/1, U XP-2698, U XP-2750, U2757, and U2766 (each from Covestro).

Binder Fluids and Adhesion Promoter Fluids

As mentioned herein, to bind the particulate build material together during the build process to form a 3D intermediate part, a binder fluid can be applied to the particulate build material on a layer by layer basis. In some examples, the binder fluid can include polymer particles as a binding agent and an aqueous liquid vehicle. In other examples, the binder fluid can also include a blocked polyisocyanate adhesion promoter. If the binder fluid also includes the blocked polyisocyanate adhesion promoter described herein, then there may or may not be a separate adhesion promoter fluid. If the blocked polyisocyanate adhesion promoter is not present in the binder fluid, then examples of the 3D printing kit disclosed herein include a separate adhesion promoter fluid that contains the blocked polyisocyanate adhesion promoter. In other words, the blocked polyisocyanate adhesion promoter and the polymer particles are included in the examples disclosed herein i) either together in a common binder fluid, or ii) in separate fluids as a binder fluid and an adhesion promoter fluid, or ii) the blocked polyisocyanate adhesion promoter can be included with the polymer particles in the common binder fluid and there may still further be a separate adhesion promoter fluid.

As such, as used herein, the term "binder fluid" refers to a fluid that includes water and polymer particles that are effective for binding layers of particulate build material when forming a 3D intermediate part. Examples of the binder fluid can also include the blocked polyisocyanate adhesion promoter, particularly if there is not a separate adhesion promoter fluid present. Moreover, the term "adhesion promoter fluid" refers to a fluid that includes water and the blocked polyisocyanate adhesion promoter. The adhesion promoter fluid may or may not be present in a 3D printing kit or related methods of 3D printing, as the blocked polyisocyanate adhesion promoter may already be present in the binder fluid. Still further, the term "fluid" does not infer that the composition is free of particulate solids, but rather, can include solids dispersed therein, including carbon black pigment or disperse dyes, polymer particles, or other dispersed solids.

Regardless of whether the binder fluid delivers both the polymer particles and the blocked polyisocyanate adhesion promoter to the particulate build material, or whether the binder fluid delivers the polymer particles and a separate adhesion promoter fluid delivers the blocked polyisocyanate adhesion promoter, there are weight ratios of polymer particles to blocked polyisocyanate adhesion promoter within a layer of the particulate build material that can be effective for enhancing tensile strength of the 3D intermediate object prior to sintering. For example, the weight ratio of polymer particles to blocked polyisocyanate adhesion promoter when applied to the particulate build material can be from about 5:1 to about 100:1, from about 9:1 to about 55:1, or from about 17:1 to about 50:1. If there are two fluids used, namely a binder fluid and an adhesion promoter fluid, these fluids can be formulated to deliver the polymer particles from the binder fluid and the blocked polyisocyanate adhesion promoter from the adhesion promoter fluid at a binder fluid to adhesion promoter weight ratio of about 5:1 to about 1:5, from about 2:1 to about 1:2, or at about 1:1, depending upon the amounts of the polymer particles and adhesion promoter in the separate fluids, as well as the desired ratio of the polymer particles and adhesion promoter when applied to the particulate build material. The respective fluids can be formulated to deliver volumes of fluid sufficient so that some mixing can occur when applied to the particulate build material.

Regardless of where the polymer particles reside relative to the blocked polyisocyanate adhesion promoter, the fluids disclosed herein can be aqueous fluids in the form of aqueous dispersions or solutions carried by an aqueous liquid vehicle. As used herein, the term "aqueous liquid vehicle" may refer to i) the liquid fluid to which the polymer particles and the blocked polyisocyanate adhesion promoter are added to form one example of the binder fluid, or ii) the liquid fluid to which the polymer particles are added to form another example of the binder fluid, or iii) the liquid fluid to which the blocked polyisocyanate adhesion promoter is added to form an example of the separate adhesion promoter fluid.

The aqueous liquid vehicle can make up about 60 wt % to about 90 wt % of the binder fluid (with or without the blocked polyisocyanate adhesion promoter). In other examples, the aqueous liquid vehicle can be included in the binder fluid at from about 60 wt % to about 85 wt %, from about 60 wt % to about 80 wt %, from about 75 wt % to about 90 wt %, or from about 70 wt % to about 80 wt %, based on a total weight of the binder fluid. If there is a separate adhesion promoter fluid, the aqueous liquid vehicle of this fluid can make up about 80 wt % to about 99.9 wt % of the adhesion promoter fluid. In further detail, if there is a separate adhesion promoter fluid, the aqueous liquid vehicle can be included in this fluid at from about 80 wt % to about 99 wt %, from about 80 wt % to about 95 wt %, from about 90 wt % to about 98 wt %, or from about 85 wt % to about 95 wt %, based on a total weight of the adhesion promoter fluid.

In examples of the binder fluid, the polymer particles can be present, based on a total weight of the binder fluid, in an amount ranging from about 1 wt % to about 40 wt %. In other more detailed examples, the polymer particles can be present at from about 5 wt % to about 30 wt %, from about 12 wt % to about 22 wt %, from about 15 wt % to about 20 wt %, from about 10 wt % to about 20 wt %, or from about 6 wt % to about 18 wt %, based on the total weight of the binder fluid. These weight percentages represent active solid polymer particle amounts, and do not account for any water or other non-active components that may be part of a polymer particle dispersion that is added to the binder fluid.

In examples of the binder fluid that also include the blocked polyisocyanate adhesion promoter, the blocked polyisocyanate adhesion promoter can be present, based on a total weight of the binder fluid, in an amount ranging from about 0.05 wt % to about 5 wt %. In other more detailed examples, the blocked polyisocyanate adhesion promoter can be present at from about 0.3 wt % to about 3 wt %, from about 0.6 wt % to about 2 wt %, or from about 0.9 wt % to about 1.5 wt %, based on the total weight of the binder fluid. These weight percentages represent active blocked polyisocyanate amounts, and do not account for any water or other non-active components that may be part of a blocked polyisocyanate solution or dispersion that is added to the binder fluid.

In examples of the adhesion promoter fluid (that is separate from the binder fluid), the blocked polyisocyanate adhesion promoter can be present, based on a total weight of the adhesion promoter fluid, in an amount ranging from about 0.1 wt % to about 10 wt %. In other more detailed examples, the blocked polyisocyanate adhesion promoter can be present at from about 0.3 wt % to about 8.5 wt %, from about 2 wt % to about 7 wt %, or from about 0.9 wt % to about 5 wt %, based on the total weight of the adhesion promoter fluid. These weight percentages represent active blocked polyisocyanate amounts, and do not account for any water or other non-active components that may be part of a blocked polyisocyanate solution or dispersion that is added to the adhesion promoter fluid.

Whether the blocked polyisocyanate is used together with polymer particles in the binder fluid or is used in a separate fluid, water soluble diol(s), triol(s), diamine(s), triamine(s), and/or waterborne polyol dispersion(s) can be used together with blocked polyisocyanate to enhance the crosslinking density. The amount of any of these components may range from 0 wt % to about 50 wt % based on the weight of the blocked polyisocyanate, or from about 5 wt % to about 40 wt % based on the weight of the blocked polyisocyanate, or from about 5 wt % to about 30 wt % based on the weight of the blocked polyisocyanate.

The aqueous liquid vehicle of the binder fluid (with or without the blocked polyisocyanate adhesion promoter) and/or the separate adhesion promoter fluid can include water, co-solvent(s), surfactant(s) and/or dispersing agent(s), antimicrobial(s), viscosity modifier(s), pH adjuster(s), sequestering agent(s), and the like. In one example, water can be present at from about 30 wt % to 100 wt % of the aqueous vehicle component—excluding polymer binder and blocked polyisocyanate adhesion promoter—based on a total weight of the aqueous liquid vehicle. In other examples, the water can be present at from about 60 wt % to about 95 wt %, from about 75 wt % to 100 wt %, or from about 80 wt % to about 99 wt %, based on a total weight of the aqueous liquid vehicle.

The co-solvent can be present at from about 0.5 wt % to about 50 wt % in the aqueous liquid vehicle, based on a total weight of the binder fluid or the total weight of the adhesion promoter fluid. In some examples, the co-solvent can be a high boiling point solvent, which can have a boiling point of at least about 110° C. Example co-solvents can include aliphatic alcohols, aromatic alcohols, alkyl diols, glycol ethers, polyglycol ethers, lactams, formam ides, acetamides, long chain alcohols, and combinations thereof. For example, the co-solvent can include aliphatic alcohols with a —$CH_2OH$ group, secondary aliphatic alcohols, 1,2-alcohols, 1,3-alcohols, 1,5-alcohols, ethylene glycol alkyl ethers, propylene glycol alkyl ethers, C6 to C12 homologs of polyethylene glycol alkyl ethers, N-alkyl caprolactams, unsubstituted caprolactams, 2-pyrrolidone, 1-methyl-2-pyrrolidone, N-(2-hydroxyethyl)-2-pyrrolidone, both substituted and unsubstituted formam ides, both substituted and unsubstituted acetam ides, combinations thereof, and the like. Other example organic co-solvents can include propyleneglycol ether, dipropyleneglycol monomethyl ether, dipropyleneglycol monopropyl ether, dipropyleneglycol monobutyl ether, tripropyleneglycol monomethyl ether, tripropyleneglycol monobutyl ether, dipropyleneglycol monophenyl ether, 2-pyrrolidone, 2-methyl-1,3-propanediol (MP-diol), 1,2-butanediol, and combinations thereof.

If a surfactant is included, examples can include SURFYNOL® SEF (a self-emulsifiable wetting agent based on acetylenic diol chemistry), SURFYNOL® 104 (a non-ionic wetting agent based on acetylenic diol chemistry), or SURFYNOL® 440 (an ethoxylated low-foam wetting agent) (all available from Evonik Industries AG, Germany); TERGITOL® TMN-6 (a branched secondary alcohol ethoxylate, non-ionic surfactant), TERGITOL® 15-S-5 or TERGITOL® 15-S-7 (each of which is a secondary alcohol ethoxylate, non-ionic surfactant), or DOWFAX® 2A1 or DOWFAX® 8390 (each of which is an alkyldiphenyloxide disulfonate, available from Dow, USA); CAPSTONE® FS-35 (non-ionic fluorosurfactant from DuPont, USA) or a combination thereof. The surfactant or combinations of surfactants can be present in the binder fluid and/or the adhesion promoter fluid at from about 0.1 wt % to about 5 wt % in its respective fluid based on the total fluid content weight, and in some examples, can be present at from about 0.5 wt % to about 2 wt %. These weight percentages represent active surfactant amounts, and do not account for any water or other non-active components that may be part of a surfactant solution or dispersion that is added to the binder fluid and/or the separate adhesion promoter fluid.

With respect to antimicrobials, any compound suitable to inhibit the growth of harmful microorganisms can be included. These additives may be biocides, fungicides, and other microbial agents. Examples of suitable antimicrobials can include NUOSEPT® (Troy, Corp.), UCARCIDE™, KORDEK™, ROCIMA™, KATHON™ (all available from The Dow Chemical Co.), VANCIDE® (R.T. Vanderbilt Co.), PROXEL® (Arch Chemicals), ACTICIDE® B20 and ACTICIDE® M20 and ACTICIDE® MBL (blends of 2-methyl-4-isothiazolin-3-one (MIT), 1,2-benzisothiazolin-3-one (BIT), and Bronopol (Thor Chemicals); AXIDE™ (Planet Chemical); NIPACIDE™ (Clariant), etc. In an example, the binder fluid and/or the separate adhesion promoter fluid may include a total amount of antimicrobials that ranges from about 0.0001 wt % to about 1 wt %. These weight percentages represent active antimicrobial amounts, and do not account for any water or other non-active components that may be part of an antimicrobial solution or dispersion that is added to the binder fluid and/or the separate adhesion promoter fluid.

Sequestering agents (or chelating agents) such as EDTA (ethylene diamine tetra acetic acid) may be included to eliminate the deleterious effects of heavy metal impurities, and buffer solutions may be used to control the pH of the binder fluid and/or the adhesion promoter fluid. Whether a single chelating agent is used or a combination of chelating agents is used, the total amount of chelating agent(s) in the binder fluid and/or the separate adhesion promoter fluid may range from greater than 0 wt % to about 2 wt % based on the total weight of the binder fluid and/or the separate adhesion promoter fluid. These weight percentages represent active sequestering/chelating agent amounts, and do not account for any water or other non-active components that may be part of a sequestering agent solution or dispersion that is added to the binder fluid and/or the separate adhesion promoter fluid.

Viscosity modifiers and buffers may also be present, as well as other additives to modify properties of the respective fluids.

In some examples, the aqueous liquid vehicle(s) can also include from about 0.1 wt % to about 1 wt % of an anti-kogation agent, based on a total weight of the binder fluid (with or without the blocked polyisocyanate adhesion promoter) or the total weight of the adhesion promoter fluid. These weight percentages represent active anti-kogation agent amounts, and do not account for any water or other non-active components that may be part of an anti-kogation agent solution or dispersion that is added to the binder fluid and/or the separate adhesion promoter fluid. Kogation refers to the deposit of dried solids on a printhead. An anti-kogation agent can be included to prevent the buildup of dried solids on the printhead. Examples of suitable anti-kogation agents can include oleth-3-phosphate (commercially available as CRODAFOS™ O3A or CRODAFOS™ N-3 acid), dextran 500k, CRODAFOS™ HCE (phosphateester from Croda Int.), CRODAFOS® N10 (oleth-10-phosphate from Croda Int.), or DISPERSOGEN® LFH (polymeric dispersing agent with aromatic anchoring groups, acid form, anionic, from Clariant), etc.

Three-dimensional Printing Kits, Multi-Fluid Kits for Three-dimensional Printing, and Methods of Three-dimensional Printing As used herein, a "material set" or "kit" can be synonymous with and understood to include a plurality of compositions comprising one or more components where the different compositions can be separately contained in one or more containers prior to and/or during use, e.g., building a green 3D object for subsequent fusing. These compositions of the "kit" can be combined together during a 3D build process. The containers can be any type of a vessel, box, or receptacle made of any material Referring now to FIG. 1A, a 3D printing kit 100 is schematically shown and can include a particulate build material 110 including from about 80 wt % to 100 wt % metal particles based on the total weight of the particulate build material; and a binder fluid 120 including water, polymer particles in an amount of from about 10 wt % to about 40 wt % based on the total weight of the binder fluid, and a blocked polyisocyanate adhesion promoter in an amount of from about 0.05 wt % to about 5 wt % based on the total weight of the binder fluid.

Referring now to FIG. 1B, a multi-fluid kit 101 for 3D printing is schematically shown and can include a binder fluid 120' including water and polymer particles in an amount of from about 1 wt % to about 40 wt % based on the total weight of the binder fluid, and a separate adhesion promoter fluid 130 including water and a blocked polyisocyanate adhesion promoter in an amount of from about 0.1 wt % to about 15 wt % based on the total weight of the adhesion promoter fluid. In this example, the multi-fluid kit 101 may be included in a 3D printing kit 100', which further includes a particulate build material 110 including from about 80 wt % to 100 wt % metal particles based on the total weight of the particulate build material 110.

Thus, the 3D printing kits 100, 100' include the particulate build material 110, and the printing kits 100, 100' further include one or two fluids 120 or 120' and 130 to deliver polymer particles and blocked polyisocyanate adhesion promoter to the particulate build material 110. In examples where there is a separate adhesion promoter fluid 130, the blocked polyisocyanate adhesion promoter can be in both fluids 120', 130 or simply in the adhesion promoter fluid 130 (and thus not in the binder fluid 120').

FIG. 2 illustrates an example of the 3D printing kit 100 in use. In this example, the particulate build material 110 is deposited from a particulate build material source 108 onto a build platform 102 where it can be flattened or smoothed, such as by a mechanical roller or other flattening mechanism or technique. In this example, the binder fluid 120 includes both the polymer particles and the blocked polyisocyanate adhesion promoter. The binder fluid 120 can be ejected onto the particulate build material 110 from a fluid ejector 104 (such as a thermal inkjet printhead or a piezoelectric inkjet printhead), for example, to provide for selective patterning of the particulate build material 110. The location(s) of the selective applied binder fluid can be selected to correspond with a layer of a 3D printed object, such as from a 3D object model or computer model. The patterned portion(s) of the layer of the particulate build material 110 are shown at reference numeral 124.

Heat (h) can be used, such as from a heat source 112, at the various layers (or group of layers) to remove water from the binder fluid 120. This temperature is 100° C. or less. In one example, heat can be applied from overhead, e.g., prior to application of the next layer of particulate build material, or after multiple layers are formed, etc.), and/or can be provided by the build platform 102 from beneath the particulate build material 110 and/or from the particulate build material source 108 (which preheats the particulate build material 110 prior to dispensing it on the build platform 102 or a previously applied and patterned layer.

After individual layers are patterned with binder fluid 120, which in this example includes both the polymer particle binder material and the blocked polyisocyanate adhesion promoter, the build platform 102 can be dropped a distance of (x), which can correspond to at least the thickness of a patterned layer, so that another layer of the particulate build material 110 can be added thereon and patterned with the binder fluid 120, etc. The process can be repeated on a layer by layer basis until all of the desired layers are patterned in accordance with a 3D object model.

After all of the desired layers of particulate build material 110 are patterned with the binder fluid 120, heating all of the individually patterned layers is performed. This heating is performed at a temperature ranging from about 120° C. to about 200° C. This higher temperature heating at least substantially removes water and co-solvents, cures the polymer particles, and also deblocks the polyisocyanate to free isocyanate group(s) that react to form the crosslinked network. As such, heating all of the individually patterned layers forms a crosslinked network among the metal particles in the patterned portions 124 of all of the individually patterned layers, thereby forming a 3D intermediate object. The now cured portions form the 3D intermediate object, and any non-patterned build material surrounding the 3D intermediate object remains non-cured.

The 3D intermediate part, in this example, includes a 3D object formed of cured/solidified 3D intermediate part layers, which include both particulate build material and a crosslinked network holding the particulate build material together. The 3D intermediate part is formed that is stable enough to be moved to an oven (or other heating device) suitable for de-binding sintering e.g., annealing, melting, fusing, or the like.

FIG. 3 illustrates another example of the 3D printing kit 100' in use. As described in reference to FIG. 2, the particulate build material 110 is deposited from a particulate build material source 108 onto a build platform 102 where it can be flattened or smoothed. In this example, the binder fluid 120' includes the polymer particles, but the blocked polyisocyanate adhesion promoter is delivered from a separate adhesion promoter fluid 130. The separate fluids 120', 130 can be separately ejected onto the particulate build material 110 from respective fluid ejectors 104, 106. To provide for selective pattering of the particulate build material 110, the location of the binder fluid 120 and adhesion promoter fluid 130 can correspond with a layer of a 3D printed object, such as from a 3D object model or computer model.

The patterned portions are shown at 124' in FIG. 3. Also shown in FIG. 3 is an intermediate layer 122 which includes the particulate build material 110 and the binder 120' fluid, as the adhesion promoter fluid 130 (in this example) has not yet come into contact with this intermediate layer 122. It should be noted that when there are two separate fluids 120', 130, one which carries polymer binder and another that carries the blocked polyisocyanate adhesion promoter, the blocked polyisocyanate adhesion promoter does not necessarily need to be applied to every place that the binder fluid is applied. For example, it may be the case that the adhesion promoter fluid 130 could be reserved for areas where additional binding strength may be desired, and not used at other locations where the binder fluid 120' is sufficient to provide the binding strength. Small detailed portions of a 3D intermediate part may benefit from additional adhesion or tensile strength; whereas, in the center or core of 3D intermediate part, the polymer particles may be sufficient to provide binding without the use of the blocked polyisocyanate adhesion promoter. Thus, the use of two separate fluids 120', 130 provides some additional flexibility with respect to modulating binding strength or tensile strength for use on an as desired basis.

As shown in FIG. 3, heat (h) can be used, such as from a heat source 112, at the various layers (or group of layers) to remove water. This temperature is 100° C. or less. In one example, heat can be applied from overhead, e.g., prior to application of the next layer of particulate build material, or after multiple layers are formed, etc.), and/or can be provided by the build platform 102 from beneath the particulate build material 110.

After individual layers are patterned with binder fluid 120' and adhesion promoter fluid 130, the build platform can be dropped a distance of (x), which can correspond to at least the thickness of a patterned layer, so that another layer of the particulate build material 110 can be added thereon and patterned with additional binder fluid 120 and adhesion promoter fluid 130. The process can be repeated on a layer by layer basis all of the desired layers are patterned in accordance with a 3D object model.

After all of the desired layers of particulate build material 110 are patterned with the binder fluid 120' and the adhesion promoter fluid 130, heating all of the individually patterned layers is performed. This heating is performed at a temperature ranging from about 120° C. to about 200° C. This higher temperature heating at least substantially removes water and co-solvents, cures the polymer particles, and also deblocks the polyisocyanate to free isocyanate group(s) that react to form the crosslinked network. As such, heating all of the individually patterned layers forms a crosslinked network among the metal particles in the patterned portions 124' of all of the individually patterned layers, thereby forming a 3D intermediate object. The now cured portions form the 3D intermediate object, and any non-patterned build material surrounding the 3D intermediate object remains non-cured.

The 3D intermediate part, in this example, includes a 3D object formed from cured/solidified 3D intermediate part layers, which include both particulate build material and a crosslinked network holding the particulate build material together. The 3D intermediate part that is formed is stable enough to be moved to an oven (or other heating device) suitable for de-binding and sintering e.g., annealing, melting, fusing, or the like.

The ejector(s) 104 or 104, 106 can deposit fluid(s) 120 or 120', 130 in a layer that corresponds to the layers of the 3D object, and can be used to form a 3D intermediate part in any orientation. For example, the 3D intermediate part can be printed from bottom to top, top to bottom, on its side, at an angle, or any other orientation. The orientation of the 3D intermediate part can also be formed in any orientation relative to the layering of the particulate build material 110. For example, the 3D intermediate part can be formed in an inverted orientation or on its side relative to the build layering within the particulate build material 110. The orientation of build or the orientation of the 3D intermediate part within the particulate build material 110 can be selected in advance or even by the user at the time of printing, for example.

In another example, as shown in FIG. 4, a method 200 of three-dimensional printing can include iteratively applying individual build material layers of a particulate build material which includes from about 80 wt % to 100 wt % metal particles based on the total weight of the particulate build material (reference numeral 202); based on a 3D object model, selectively applying water, polymer particles, and a blocked polyisocyanate adhesion promoter to individual build material layers to define individually patterned layers of a 3D intermediate object (reference numeral 204); and heating all of the individually patterned layers to deblock the blocked polyisocyanate adhesion promoter and form a crosslinked network among the metal particles in patterned portions of all of the individually patterned layers, thereby forming a 3D intermediate object (reference numeral 206).

The selective application of the water, polymer particles, and the blocked polyisocyanate adhesion promoter can be carried out using a single binder fluid (with the water, polymer particles, and blocked polyisocyanate adhesion promoter), or can be carried out using multiple fluids, with water and polymer particles in the binder fluid and water and the blocked polyisocyanate adhesion promoter in a separate adhesion promoter fluid. More specifically, in the former example, the polymer particles and the blocked polyisocyanate adhesion promoter can be selectively applied by ejecting a binder fluid including water. The polymer particles can be present at an amount of from about 1 wt % to about 40 wt % based on the total weight of the binder fluid and the blocked polyisocyanate adhesion promoter can be present in an amount of about 0.05 wt % to about 5 wt % based on the total weight of the binder fluid. In the latter example, the polymer particles can be selectively applied by ejecting a binder fluid including water and the polymer particles in an amount of from about 1 wt % to about 40 wt % based on the total weight of the binder fluid, and the blocked polyisocyanate adhesion promoter can be selectively applied by ejecting an adhesion promoter fluid as a separate fluid relative to the binder fluid. The adhesion promoter fluid can likewise include water, but further, the blocked polyisocyanate adhesion promoter can be present in an amount of about 0.1 wt % to about 15 wt % based on the total weight of the adhesion promoter fluid.

Following application of the binder fluid (with blocked polyisocyanate adhesion promoter included) or the binder fluid and the separate adhesion promotor fluid to all of the desired layers, the particulate build material and fluid(s) applied thereto can be heated to an elevated temperature. Heating cures the polymer particles and deblocks the polyisocyanate, which frees the isocyanate groups and enables them to react to form a crosslinked network. This crosslinked network solidifies the 3D intermediate part in preparation for moving to a sintering oven. In one example, heating to cure and crosslink can be carried out at from about 100° C. to about 250° C., about 120° C. to about 220° C., or about 140° C. to about 200° C. for time sufficient to solidify or stabilize the 3D intermediate part/object for movement to a sintering oven. Time frames for heating individual layers may be short, e.g., from about 0.5 second to about 120 seconds, for example. If heating of the 3D intermediate part occurs after it is fully formed, time frames can vary as well, depending on size of the 3D intermediate part. For example, large objects with a smaller surface to volume ratio may take longer to drive off enough fluid to stabilize the 3D intermediate part, than a smaller object with a larger surface to volume ratio. That stated, time frames for heating the 3D intermediate part after formation can be from about 10 minutes to about 8 hours, or from about 30 minutes to about 3 hours. In many cases, individual layers can be heated to temperatures at or below 100° C. during the build, and additional, high heating (120° C. to about 250° C.) can occur after patterning, in order to form the 3D intermediate part.

Upon coalescing or otherwise binding of the particulate build material by the crosslinked network, the 3D intermediate part with enhanced tensile strength can be moved to a heating device, such as a sintering oven. In one example, the heating can be a temperature ranging from about 500° C. to about 3,500° C. At lower temperatures within the range, the polymer particles and crosslinked network can thermally degrade, thereby debinding the 3D intermediate part, and at the higher temperatures within the range, the metal particles are sintered together. In another example, the de-binding and sintering temperatures can be in the range of from about 600° C. to about 1,500° C., or from about 800° C. to about 1,200° C. The de-binding temperature range can vary, depending on the polymer particle composition and the crosslinked network composition. The sintering temperature range can vary, depending on the metal particle material. In one example, the sintering temperature can range from about 10° C. below the melting temperature of the metal particles of the particulate build material to about 50° C. below the melting temperature of the metal particles of the particulate build material. In another example, the sintering temperature can range from about 100° C. below the melting temperature of the metal particles of the particulate build material to about 200° C. below the melting temperature of the metal particles of the particulate build material. The sintering temperature can also depend upon the particle size and period of time that heating occurs, e.g., at a high temperature for a sufficient time to cause particle surfaces to become physically merged or composited together. For example, a sintering temperature for stainless steel can be about 1,400° C. and an example of a sintering temperature for aluminum or aluminum alloys can range from about 550° C. to about 620° C. Temperatures outside of these ranges can be used as determined on a case by case basis.

During heating in the oven, the heating device can include an inert atmosphere to avoid oxidation of the metal particles. In one example, the inert atmosphere can be oxygen-free and can include a noble gas, an inert gas, or combination thereof. For example, the inert atmosphere can include a noble gas or an inert gas selected from argon, helium, neon, krypton, xenon, radon, or a combination thereof. Upon removal of the sintered 3D object from the oven and cooling (or annealing by controlling the cool down rate in the oven), the sintering 3D object can be treated or polished, such as by sand blasting, bead blasting, air jetting, tumble finishing such as barrel finishing, vibratory finishing, or a combination thereof. Tumble or vibratory finishing techniques can be performed wet (involving liquid lubricants, cleaners, or abrasives) or dry.

In any of the methods disclosed herein, different shaped objects may be printed in different orientations within the printing system. As such, while the object may be printed from the bottom of the object to the top of the object, it may alternatively be printed starting with the top of the object to the bottom of the object, or from a side of the object to another side of the object, or at any other orientation that is suitable or desired for the particular geometry of the part being formed.

To further illustrate the present disclosure, an example is given herein. It is to be understood that this example is provided for illustrative purposes and is not to be construed as limiting the scope of the present disclosure.

Example

To evaluate the tensile strength of various binder fluids with a blocked polyisocyanate adhesion promoter and without any blocked polyisocyanate adhesion promoter (as a control), the following binder fluid formulations were prepared, according to Table 1:

TABLE 1

| Binder Fluid Components | % Active | B0 (control) | B1 | B2 |
|---|---|---|---|---|
| 1,2-butanediol | As is | 26 | 26 | 26 |
| Tergitol ® TMN-6 | 90 | 0.3 | 0.3 | 0.3 |
| Cyan Dye* | 12.72 | 0.4 | 0.4 | 0.4 |
| Methyl Methacrylate, Styrene, Butyl Acrylate, and Methacrylic Acid Copolymer Polymer Particles (wt ratio 80/10/7/3) (Tg ~90; D50 of 200 nm) | 31 | 16 | 16 | 16 |
| Blocked polyisocyanate** | 40 | — | 1.5 | 3.00 |
| Water | | Bal. | Bal. | Bal. |

*dye is added to visually observe the binder fluid
**IMPRAFIX ® 2794

Figure 5:
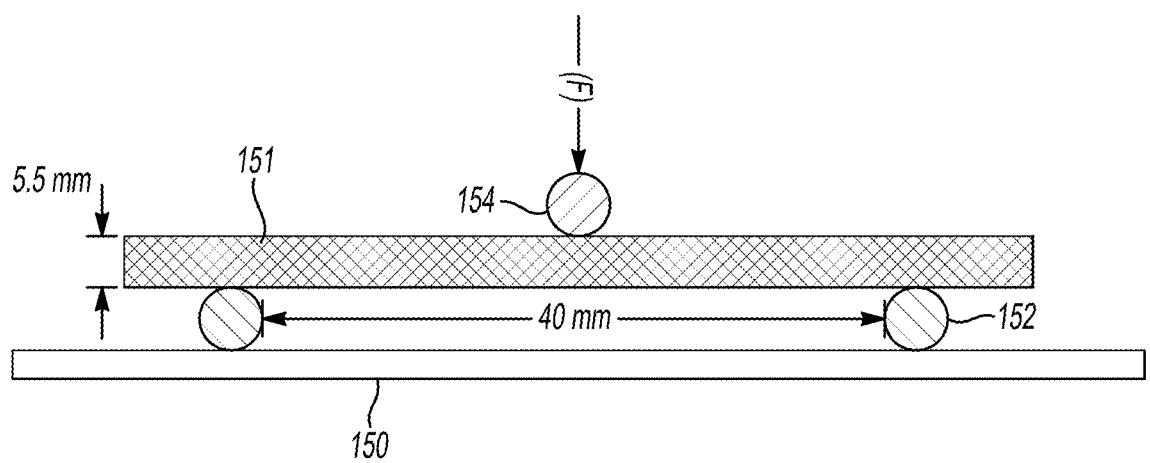
FIG. 5 illustrates an example tensile strength apparatus that can be used to evaluate tensile strength provided by various compositions for use in 3D printing kits in accordance with the present disclosure.

A tensile strength test was conducted as shown in FIG. 5, where the binder fluids prepared in accordance with Table 1 were used to prepare press bar samples 151, which were essentially solidified 3D intermediate part samples, such as those shown in FIGS. 2 and 3. The individual press bar samples included particulate build material with 100 wt % stainless steel particles having a D50 particle size of about 22 μm admixed with the various binder fluids of Table 1. To prepare the individual samples for tensile strength testing, a mixture of the stainless steel particles and various binder fluids were mixed in a high speed mixer to ensure homogenous mixing at a weight ratio of about 19:1 (94.8 wt % stainless steel particles; 5.2 wt % binder fluid) and then the wet particles/binder homogenous mixture was dried in a vacuum oven at a temperature ranging from about 30° C. to about 40° C. for two hours to remove most of the water content, leaving a dried homogenous mixture of binder solids and stainless steel particles. 18 g of the dried homogenous mixture was poured into the opening of a press bar mold and pressed under 2000 psi for 30 seconds to form the respective press bar samples. The dimension of the press bar samples, shown at 151 in FIG. 5, was 50 mm (length) by 12 mm (width) by 5.5 mm (thickness). The individual press bar samples were then carefully separated from the mold and heated in a vacuum oven. The heating conditions included two stages. The first stage included heating at 180° C. for about 10 minutes without vacuum. The second stage included heating at 180° C. at 22-25 in Hg for 30 minutes with a slow stream of air to provide for removal of solvents and some or even full curing of the polymer particle binder.

The individual cured press bar samples were then cooled and submitted to a 3-point bend INSTRON® tester, as shown by example in FIG. 5, to measure their tensile strength. The INSTRON® tester, available from Instron (USA), included a support 150, supporting pins 152, and a loading pin 154 which applied increasing force (F) to the individual press bar samples until they failed (broke under force). For the various individual press bar samples, at least five press bars were made and the average maximum tensile stress (mPa) and standard deviation were reported. The average data of this study is provided in Table 2, and the average data and standard deviation data of this study is provided in FIG. 6.

TABLE 2

| Press Bar Sample ID | Blocked Polyisocyanate* Content from Binder Fluid | Average Maximum Tensile Stress (mPa) | Standard Deviation |
|---|---|---|---|
| PB0 | 0% (Control) | 8.57 | 0.38 |
| PB1 | 1.5% | 11.1 | 0.74 |
| PB2 | 3.0% | 11.8 | 0.41 |

Figure 6:
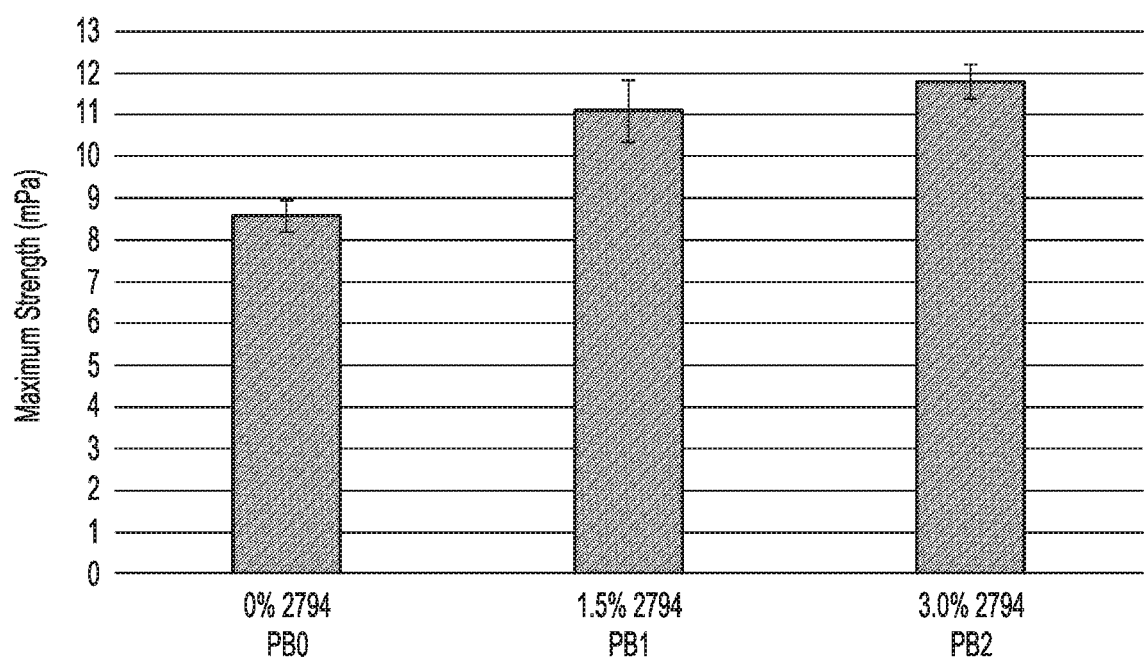
FIG. 6 is a graph showing the maximum stress to break for press bars made using examples of a binder fluid composition disclosed herein, and comparative press bars made using a comparative binder fluid composition.

***IMPRAFIX ® 2794 (shown as "2794" in FIG. 6)

Binder Fluid IDs from Table 1 correspond numerically with Press Bar Sample IDs from Table 2, e.g., B0 without a blocked polyisocyanate adhesion promoter was used to form Press Bar Sample PB0, B1 with 1.5% blocked polyisocyanate was used to prepare Press Bar Sample PB1, etc. Furthermore, the weight percentages shown in Table 2 are based on the binder fluid content, not the content present in final press bar sample.

As can be seen from Table 2 and FIG. 6, a small quantity of a blocked polyisocyanate adhesion promoter can be effective in improving the tensile stress of a press bar.

It is to be understood that the ranges provided herein include the stated range and any value or sub-range within the stated range, as if such values or sub-ranges were explicitly recited. For example, from about 500° C. to about 3,500° C. should be interpreted to include not only the explicitly recited limits of from about 500° C. to about 3,500° C., but also to include individual values, such as about 690° C., 1,000.5° C., 2,055° C., 2,750° C., etc., and sub-ranges, such as from about 900° C. to about 3,250° C., from about 525° C. to about 2,500° C., from about 1,020° C. to about 2,020° C., etc. Furthermore, the term "about" as used herein in reference to a numerical value or range, allows for a degree of variability in the value or range, for example, within 10%, or, in one aspect within 5%, of a stated value or of a stated limit of a range.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is noted that, as used in this specification and the appended claims, the singular forms "a," "an," and "the" include plural referents unless the content clearly dictates otherwise.

While several examples have been described in detail, it is to be understood that the disclosed examples may be modified. Therefore, the foregoing description is to be considered non-limiting.

What is claimed is:

1. A three-dimensional printing kit, comprising:
   a particulate build material including from about 80 wt % to 100 wt % metal particles based on a total weight of the particulate build material; and
   a separate binder fluid including:
      water;
      polymer particles in an amount ranging from about 1 wt % to about 40 wt % based on a total weight of the binder fluid, wherein the polymer particles are polymerized monomers of vinyl acetate, vinyl chloride, vinylidene chloride, vinylbenzyl chloride, vinyl ester, vinyl pyrrolidone, styrene, ethylene, maleate esters, fumarate esters, itaconate esters, α-methyl styrene, p-methyl styrene, methyl methacrylate, hexyl acrylate, hexyl methacrylate, hydroxyethyl acrylate, butyl acrylate, butyl methacrylate, ethyl acrylate, ethyl methacrylate, propyl acrylate, propyl methacrylate, 2-ethylhexyl acrylate, 2-ethylhexyl methacrylate, octadecyl acrylate, octadecyl methacrylate, stearyl methacrylate, 2-phenoxyethyl methacrylate, vinylbenzyl chloride, isobornyl acrylate, tetrahydrofurfuryl acrylate, 2-phenoxyethyl methacrylate, benzyl methacrylate, benzyl acrylate, ethoxylated nonyl phenol methacrylate, isobornyl methacrylate, ethylene glycol dimethacrylate, diethylene glycol dimethacrylate, triethylene glycol dimethacrylate, cyclohexyl methacrylate, trimethyl cyclohexyl methacrylate, t-butyl methacrylate, n-octyl methacrylate, lauryl acrylate, lauryl methacrylate, trydecyl methacrylate, alkoxylated tetrahydrofurfuryl acrylate, isodecyl acrylate, dimethyl maleate, dioctyl maleate, acetoacetoxyethyl methacrylate, diacetone acrylamide, N-vinyl imidazole, N-vinylcarbazole, N-vinyl-caprolactam, pentaerythritol triacrylate, pentaerythritol tetra-acrylate, pentaerythritol tri-methacrylate, pentaerythritol tetramethacrylate, glycidyl acrylate, glycidyl methacrylate, tetrahydrofuryl acrylate, tetrahydrofuryl methacrylate, diacetone acrylamide, t-butyl acrylamide, divinylbenzene, 1,3-butadiene, acrylonitrile, methacrylonitrile, derivatives thereof, or mixtures thereof; and
   a blocked polyisocyanate adhesion promoter in an amount ranging from about 1.5 wt % to about 3.0 wt % based on the total weight of the binder fluid.

2. The three-dimensional printing kit as defined in claim 1 wherein the metal particles are selected from the group consisting of aluminum, aluminum alloys, titanium, titanium alloys, copper, copper alloys, cobalt, cobalt alloys, chromium, chromium alloys, nickel, nickel alloys, vanadium, vanadium alloys, tin, tin alloys, tungsten, tungsten alloys, tungsten carbide, tantalum, tantalum alloys, molybdenum, molybdenum alloys, magnesium, magnesium alloys, gold, gold alloys, silver, silver alloys, zirconium, zirconium alloys, ferrous alloys, stainless steel, steel, and an admixture thereof.

3. The three-dimensional printing kit as defined in claim 1 wherein the polymer particles have a glass transition temperature higher than 60° C. and an average particle size of 1 nm or more.

4. The three-dimensional printing kit as defined in claim 1 wherein the blocked polyisocyanate adhesion promoter is an anionic blocked polyisocyanate or a non-ionic blocked polyisocyanate.

5. The three-dimensional printing kit as defined in claim 4 wherein the blocked polyisocyanate adhesion promoter has the structure:

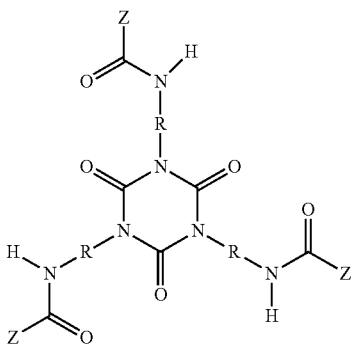

wherein:
- R is independently selected from the group consisting of a C2 to C10 branched or straight-chained alkyl, a C6 to C20 alicyclic compound, a C6 to C20 aromatic compound, and combinations thereof; and
- Z is $(BL)_{3-X}(DL)_X$, wherein BL is selected from the group consisting of a phenol blocking group, a lactam blocking group, an oxime blocking group, an azole blocking group, a diketene blocking group, a formate blocking group, and combinations thereof;
- x is from 0 to 1; and DL is an anionic or a non-ionic hydrophilic dispersing group.

6. The three-dimensional printing kit as defined in claim 1 wherein the blocked polyisocyanate adhesion promoter is a cationic blocked polyisocyanate.

7. The three-dimensional printing kit as defined in claim 1 wherein the metal particles of the particulate build material are uncoated metal particles.

8. The three-dimensional printing kit as defined in claim 1 wherein the particulate build material is devoid of a polymer resin.

9. The three-dimensional printing kit as defined in claim 1 wherein the metal particles have a D50 particle size distribution value ranging from about 0.5 μm to about 200 μm.

10. The three-dimensional printing kit as defined in claim 1 wherein the polymer particles have a core-shell morphology.

11. The three-dimensional printing kit as defined in claim 1 wherein the polymer particles are copolymer particles.

12. The three-dimensional printing kit as defined in claim 1 wherein the polymer particles have an average particle size ranging from about 100 nm to about 250 nm.

13. The three-dimensional printing kit as defined in claim 1 wherein the polymer particles have a weight average molecular weight ranging from about 5,000 Mw to about 2,000,000 Mw.

14. A three-dimensional printing kit, comprising:
- a particulate build material including from about 80 wt % to 100 wt % metal particles based on a total weight of the particulate build material; and
- a separate binder fluid including:
  - water;
  - polymer particles in an amount ranging from about 1 wt % to about 40 wt % based on a total weight of the binder fluid, wherein the polymer particles are copolymer particles of methyl methacrylate, styrene, butyl acrylate, and methacrylic acid; and
  - a blocked polyisocyanate adhesion promoter in an amount ranging from about 0.05 wt % to about 5 wt % based on the total weight of the binder fluid.

15. The three-dimensional printing kit as defined in claim 14 wherein the metal particles are selected from the group consisting of aluminum, aluminum alloys, titanium, titanium alloys, copper, copper alloys, cobalt, cobalt alloys, chromium, chromium alloys, nickel, nickel alloys, vanadium, vanadium alloys, tin, tin alloys, tungsten, tungsten alloys, tungsten carbide, tantalum, tantalum alloys, molybdenum, molybdenum alloys, magnesium, magnesium alloys, gold, gold alloys, silver, silver alloys, zirconium, zirconium alloys, ferrous alloys, stainless steel, steel, and an admixture thereof.

16. The three-dimensional printing kit as defined in claim 14 wherein the blocked polyisocyanate adhesion promoter is an anionic blocked polyisocyanate or a non-ionic blocked polyisocyanate.

17. The three-dimensional printing kit as defined in claim 16 wherein the blocked polyisocyanate adhesion promoter has the structure:

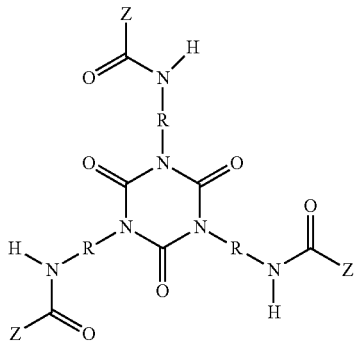

wherein:
- R is independently selected from the group consisting of a C2 to C10 branched or straight-chained alkyl, a C6 to C20 alicyclic compound, a C6 to C20 aromatic compound, and combinations thereof; and
- Z is $(BL)_{3-X}(DL)_X$, wherein BL is selected from the group consisting of a phenol blocking group, a lactam blocking group, an oxime blocking group, an azole blocking group, a diketene blocking group, a formate blocking group, and combinations thereof; x is from 0 to 1; and DL is an anionic or a non-ionic hydrophilic dispersing group.

18. The three-dimensional printing kit as defined in claim 14 wherein the blocked polyisocyanate adhesion promoter is a cationic blocked polyisocyanate.

* * * * *